United States Patent [19]

Urfer et al.

[11] Patent Number: 5,242,615
[45] Date of Patent: Sep. 7, 1993

[54] ANIONIC AND AMPHOTERIC SURFACTANT COMPOSITIONS WITH REDUCED VISCOSITY

[75] Inventors: Allen D. Urfer, Lansdale; Virginia Lazarowitz, Hatfield, both of Pa.

[73] Assignee: Henkel Corporation, Ambler, Pa.

[21] Appl. No.: 644,470

[22] Filed: Jan. 18, 1991

Related U.S. Application Data

[63] Continuation of Ser. No. 406,992, Sep. 14, 1989, abandoned.

[51] Int. Cl.$^5$ ............................................. C11D 3/382
[52] U.S. Cl. ............................. 252/174.17; 252/174.25
[58] Field of Search ........................ 252/174.17, 174.25

[56] References Cited

U.S. PATENT DOCUMENTS

| | | | |
|---|---|---|---|
| 3,920,563 | 11/1975 | Wixon | 252/8.75 |
| 3,954,679 | 4/1976 | Wixon | 252/555 |
| 3,985,687 | 10/1976 | Inamorato | 252/551 |
| 4,212,749 | 7/1980 | Kolbe | 252/8.75 |
| 4,488,981 | 12/1984 | Urfer | 252/174.17 |
| 4,668,422 | 5/1987 | Malik et al. | 252/174.17 |
| 4,675,127 | 6/1987 | Kickle et al. | 252/174.17 |
| 4,713,447 | 12/1987 | Letton | 536/18.6 |
| 4,715,991 | 12/1987 | Hirakouchi | 252/555 |
| 4,732,696 | 3/1988 | Urfer | 252/174.17 |
| 4,839,098 | 6/1989 | Wisotzki et al. | 252/557 |

FOREIGN PATENT DOCUMENTS 0280143 2/1988 European Pat. Off. .

OTHER PUBLICATIONS

"Liquid or Soft Soap"; Household & Personal Products Industry, Oct. 1990, pp. 51–53.
Synthetic Detergents; 7th Ed., Davidsohn & Milwidsky, p. 68.

*Primary Examiner*—Paul Lieberman
*Assistant Examiner*—Kery A. Fries
*Attorney, Agent, or Firm*—Ernest G. Szoke; Wayne C. Jaeschke; Daniel S. Ortiz

[57] ABSTRACT

The invention is a composition of at least one anionic or amphoteric surfactant, water and a viscosity reducing effective amount at least one alkyl polyglycoside and at least one alkali metal chloride.

14 Claims, No Drawings

ANIONIC AND AMPHOTERIC SURFACTANT COMPOSITIONS WITH REDUCED VISCOSITY

This application is a continuation of application Ser. No. 07/406,922 filed on Sep. 14, 1989 now abandoned.

BACKGROUND OF THE INVENTION

1. Field of the Invention

The invention is an anionic or amphoteric surfactant composition with reduced viscosity. The composition is a mixture of a surfactant and a viscosity reducing amount of an alkyl polyglycoside and alkali metal chloride.

Anionic surfactants and amphoteric surfactants are known materials which have many uses. They are generally sold in a mixture with water containing from about 30 to about 80% surfactant. The mixture can also contain hydrotropes which make the surfactant compatible with water and reduce viscosity. Generally as the amount of surfactant in the mixture exceeds about 30% by weight, the mixture becomes more viscous until a paste like mixture or gel is formed. It would be useful to provide a means for reducing the viscosity of aqueous surfactant mixtures so that the mixtures could be shipped at higher surfactant concentrations and higher surfactant concentrations could be transferred in plant processes. At concentrations above about 50% by weight, aqueous solutions of anionic and amphoteric surfactants have the character of viscous liquids, gels or pasty solids.

In some applications, the surfactants are spray dried to provide a powder material which can be blended with other dry materials to prepare a detergent formulation. It would be useful to provide a pumpable composition with a higher concentration of surfactant so that a higher throughput of the spray dryer can be obtained.

2. Statement of the Related Art

It is known that the addition of alkyl polyglycosides to a phosphate built aqueous crutcher slurry can reduce the viscosity of the slurry (U.S. Pat. No. 4,675,127). U.S. patent application Ser. No. 07/260,646 discloses that the addition of an alkyl polyglycoside and an alkali metal chloride to a carbonate containing crutcher slurry, reduces the viscosity of the slurry.

It is also known that addition of an alkyl glycoside and ammonium chloride to an aqueous liquid detergent formulation can increase the viscosity of the formulation (U.S. Pat. No. 4,732,696). U.S. patent application Ser. No. 07/353,723 discloses that the addition of an alkyl polyglycoside and an alkali metal chloride within a critical range increases the viscosity of certain liquid sulfosuccinate detergent compositions. U.S. Pat. No. 4,488,981 discloses that the addition of alkyl mono and polyglucosides having alkyl groups with six (6) carbon atoms or less in the alkyl group, to aqueous mixtures of anionic or anionic and nonionic surfactants in water lowers the viscosity of the mixture.

BRIEF DESCRIPTION OF THE INVENTION

Other than in the operating examples, or where otherwise indicated, all numbers expressing quantities of ingredients or reaction conditions used herein are to be understood as modified in all instances by the term "about".

According to the invention, the viscosity of an aqueous anionic or amphoteric surfactant composition, at a concentration of from about 30 to 80% by weight of surfactant, can be reduced by adding a viscosity reducing amount of a combination of an alkyl polyglycoside and alkali metal chloride to the composition.

The amount of the alkyl polyglycoside which is added to the composition generally ranges from about 0.1 to about 10% by weight of the surfactant, water and the alkyl polyglycoside metal chloride mixture. Preferably, the amount of the alkyl polyglycoside added to the composition is in a range from about 0.25 to about 5% by weight and more preferably from about 0.5 to about 3% by weight of the mixture.

The amount of alkali metal chloride which is added to the composition is in the range of from about 0.1 to about 10% and preferably from about 0.5 to about 5% by weight of the mixture and most preferably from about 0.75 to about 3% by weight of the mixture.

The amount of the alkyl polyglycoside and alkali metal chloride which is added to the aqueous surfactant mixture is determined by the nature of the surfactant and the reduction in viscosity which is required.

DETAILED DESCRIPTION OF THE INVENTION

The anionic surfactants whose viscosity can be reduced by addition of an alkyl polyglycoside and an alkali metal chloride, includes any of the common surfactants which are classified as anionic surfactants. The surfactants include the alkali metal, ammonium and magnesium salts of the alpha olefin sulfonates, alkyl sulfonates, alkyl aryl sulfonates, alkyl aryl ether sulfates, alkyl ether sulfates, sulfated alcohol ethoxylates, taurates, petroleum sulfonates, alkyl napthalene sulfonates, alkyl sarcosinates and the alkyl sulfosuccinates.

Typical surfactants which fall within the above description include sodium lauryl sulfonate, ammonium lauryl sulfonate, dodecyl benzene sulfonate, sodium lauryl ether sulfate, diethanolamine lauryl sulfate, ammonium salts of sulfated alcohol ethoxylates, sodium cocoyl isethionate, sodium N-methyl-N-oleoyl taurate, sodium N-methyl-N-cocoyl taurate, triethanolamine lauryl sulfate, disodium monooleamide PEG-2 sulfosuccinate, petroleum sulfonates sodium salt, alkyl napthalene sodium sulfonates, sodium lauroyl sarcosinate, and sodium alkyl sulfosuccinate.

The amphoteric surfactants whose aqueous solution viscosities can be reduced include the betaines, the sultaines, the imidazoline derivatives and the like.

Typical amphoteric surfactants include ricinoleamidopropyl betaine, cocamidopropyl betaine, stearyl betaine, stearyl amphocarboxy glycinate, sodium lauraminopropionate, cocoamidopropyl hydroxy sultaine, disodium lauryliminodipropionate, tallowiminodipropionate, cocoampho- carboxy glycinate, cocoimidazoline carboxylate, lauric imidazoline monocarboxylate, lauric imidazoline dicarboxylate, lauric myristic betaine, cocoamidosulfobetaine, alkylamidophospho betaine and the like.

The above list of anionic and amphoteric surfactants is not intended to be all encompassing but is illustrative of the types of surfactants the viscosity of which aqueous mixtures can be reduced by the introduction of an alkyl polyglycoside and alkali metal chloride into the mixture. The mixture of surfactant and water is generally a liquid with a high viscosity, a gel or a pasty material at concentrations in the range of about 30–80% by weight. The viscosity of the mixture can be substantially reduced by the addition of an alkyl polyglycoside and an alkali metal chloride to the surfactant mixture with water.

The present invention is particularly useful in that the alkyl polyglycoside which is added to the surfactant is also a surfactant and therefore the composition contains less non-surfactant material than is generally required in the prior art. In the prior art, the viscosity is reduced by the addition of certain hydrotrope agents which aid in dissolving the material in the water and reducing the viscosity.

The aliphatic polyglycoside surfactants useful in the practice of the present invention are nonionic surfactants of the formula $RO(R_1O)_mG_r$ wherein R is an alkyl or alkenyl group having from about 8 to about 22 carbon atoms and preferably from about 10 to 18 carbon atoms. The aliphatic group can be alkyl or alkenyl but is preferably unbranched alkyl. As used in the present invention the phrase alkyl polyglycoside is intended to encompass both the alkyl and alkenyl polyglycosides. $R_1$ is an alkyl group having 2 or 3 carbon atoms, m is a number from 0 to 10 and preferably 0. G is the residue of a reducing saccharide and r is a number of from about 1.05 to about 10 and preferably about 1.1 to about 2. The r is the average degree of polymerization of the saccharide (DP).

The aliphatic polyglycosides are known compositions and can be prepared by the method disclosed in U.S. Pat. No. 4,713,447 which is incorporated herein by a reference.

The saccharides useful for preparing the aliphatic polyglycoside used in the practice of the present invention, are reducing monosaccharides or materials which can form reducing monosaccharides during the process for preparing the polyglycoside composition. The reducing saccharides include hexoses and pentoses. Typical examples of monosaccharides includes glucose, mannose, galactose, gulose, talose, altrose, allose, idose, arabinose, xylose, ribose, lyxose and the like. More for reasons of its low cost and ready availability, glucose is a preferred saccharide. The aliphatic polyglycosides are present in the composition of the present invention in ranges from about 0.1 to about 10% by weight, preferably from about 0.5 to about 5% by weight and most preferably about 0.75% to about 3% by weight of the mixture.

The alkali metal chloride useful in the practice of the present are typically lithium chloride, sodium chloride and potassium chloride, preferably the alkali metal chloride is sodium chloride or potassium chloride.

A composition of the present invention requires a small but viscosity reducing effective amount of the alkali metal chloride. Generally, the alkali metal chloride is present from about 0.1 to about 10% by weight, preferably in the range of from about 0.5 to about 5% by weight and most preferably in the range of from about 0.75% to about 3.0% by weight of the composition. The amount of the alkali metal chloride included in the composition is dependent upon the particular surfactant and the amount of viscosity reduction required. Generally, it is preferred to keep the amount of alkali metal chloride in the mixture as low as possible so that the non-surfactant materials in the composition is maintained at a low level. However, if the alkali metal chloride is not objectionable in the subsequent use of mixture, any amount which aides in reducing the viscosity is suitable. At higher levels alkali metal chlorides are known to increase the viscosity of some surfactant mixtures.

The composition of the present invention consists essentially of the surfactant, the alkyl polyglycoside, the alkali metal chloride and water. However, under particular conditions, especially where spray drying of the surfactant is contemplated, it may be useful to include certain filler materials to provide a dry solid product. The present invention is not intended to be a viscosity reducing agent for a crutcher slurry as such since the product consists essentially of the surfactant, the alkyl polyglycoside, the alkali metal chloride and optionally a filler material. A filler material is generally a water soluble salt which does not assist the detergent properties.

The present invention will be illustrated by way of the following examples. In the examples, a composition was prepared containing the surfactant and water. A second composition was prepared containing the surfactant, and a viscosity reducing amount of the alkyl polyglycoside and the alkali metal chloride and water. The viscosities of the various mixtures were measured at 25° C. with a Brookfield viscosimeter using a No. 4 spindle at 10 RPM.

EXAMPLE 1

A composition was prepared containing 43% by weight of a sodium salt of an alpha olefin sulfonate wherein the alpha olefin contained from 14 to 16 carbon atoms. An aqueous mixture of the alpha olefin sulfonate was prepared by mixing 56.8 grams of the surfactant (88% active material) and 58.2 grams of water. The mixture had a viscosity above 50,000 CPS.

A mixture was prepared by mixing 56.8 grams of the surfactant as above, 58.2 grams of water, 2.0 grams of a 50% by weight aqueous solution of APG®500 (an alkyl polyglucoside with an alkyl group having 12–13 carbon and a degree of polymerization (DP) of 1.4) and 2.5 grams of sodium chloride. The viscosity of the mixture was 14,000 CPS.

EXAMPLE 2

A mixture was prepared containing 38% of a sodium salt of a 12–13 carbon alkyl ether sulfate containing 2 moles of ethylene oxide. The mixture was prepared by mixing 81.6 grams of a 47% active solution of the alkyl ether sulfate with 18.4 grams of water. The viscosity of the mixture was greater than 50,000 CPS.

A mixture was prepared by mixing 81.6 grams of a 47% active solution of the alkyl ether sulfate used above, 18.4 grams of water, 2 grams of a 50% by weight aqueous solution of APG®500 and 2.5 grams of sodium chloride. The viscosity of the mixture was 4,840 CPS.

EXAMPLE 3

An aqueous mixture was prepared containing 43% by weight of sodium lauryl sulfate. The mixture was prepared by mixing 89.3 grams of an aqueous mixture containing 56% by weight of lauryl sulfate with 25.2 grams of water. The mixture had a viscosity greater than 50,000 CPS.

A second mixture was prepared by mixing 89.3 grams of the aqueous lauryl sulfate mixture having 56% by weight of lauryl sulfate with 25.2 grams of water, 2 grams of a 50% by weight aqueous solution of APG®500 and 2.5 grams of sodium chloride. The viscosity of the mixture was 16,100 CPS.

EXAMPLE 4

A mixture was prepared containing 63% by weight of the sodium salt of 12-13 carbon alkyl ether sulfate containing 3 moles of EO. The viscosity of the mixture was greater than 50,000 CPS.

A second mixture was prepared containing 100 grams of a 63% by weight solution of the sodium salt of the 12-13 carbon alkyl ether sulfate used above, 2 grams of a 50% by weight aqueous solution of APG ®500 and 2.5 grams of sodium chloride. The viscosity of the mixture was 2,400 CPS.

It is clear from the above examples, that the addition of small amounts of an alkyl polyglycoside and an alkali metal chloride as defined in the present invention substantially reduces the viscosity of a composition consisting essentially of an anionic or amphoteric surfactant and water.

We claim:

1. An aqueous composition consisting essentially of from about 30 to about 80% by weight of at least one anionic or amphoteric surfactant, water and a viscosity reducing effective amount of a combination of from about 0.1 to about 10% by weight of the composition of at least one alkali metal chloride and from about 0.1 to about 10% by weight of the composition of at least one alkyl polyglycoside of the formula $RO(R_1O)_m G_r$ wherein R is an alkyl group having from 8 to about 22 carbon atoms, $R_1$ is an alkyl group having 2 or 3 carbon atoms, m is a number of from 0 to 10, G is the residue of a reducing saccharide and r is a number of from about 1.05 to about 10.

2. A composition of claim 1 wherein the at least one alkyl polyglycoside comprises a composition wherein R is an alkyl group having from 10 to about 18 carbon atoms, m is 0, G is a glucose residue and r is a number of from about 1.1 to about 2.

3. A composition of claim 1 wherein the alkyl polyglycoside is present in an amount of from about 0.25 to about 5% by weight of the composition.

4. A composition of claim 2 wherein the alkyl polyglycoside is present in an amount of from about 0.25 to about 5% by weight of the composition.

5. A composition of claim 3 wherein the alkali metal chloride is present in an amount of from about 0.5 % to about 5% by weight of the composition.

6. A composition of claim 4 wherein the alkali metal chloride is present in an amount of from about 0.5% to about 5% by weight of the composition.

7. A composition of claim 1 wherein the surfactant comprises at least one salt selected from the group consisting of salts of alkyl aryl sulfonates, alkyl sulfonates, alkyl ether sulfates, alkyl sulfates, alkyl taurates, and alkyl sulfosuccinates.

8. A composition of claim 2 wherein the surfactant comprises at least one salt selected from the group consisting of salts of alkyl aryl sulfonates, alkyl sulfonates, alkyl ether sulfates, alkyl sulfates, alkyl taurates, and alkyl sulfosuccinates.

9. A composition of claim 1 wherein the surfactant is a betaine or an imidazoline derivative.

10. A composition of claim 2 wherein the amphoteric surfactant is a betaine or an imidazoline derivative.

11. A method of reducing the viscosity of a mixture consisting essentially of from about 30 to about 80% by weight of at least one anionic or amphoteric surfactant and water, which comprises; adding to the mixture a viscosity reducing effective amount of a combination of from about 0.1 to about 10% by weight of the composition of an alkali metal chloride and from about 0.1% to about 10% by weight of the composition of at least one alkyl polyglycoside of the formula $RO(R_1O)_m G_r$ wherein R is an alkyl group having from 8 to about 22 carbon atoms, $R_1$ is an alkyl group having 2 or 3 carbon atoms, G is the residue of a reducing saccharide and r is a number of from about 1.05 to about 10 and m is a number of from 0 to 10.

12. A method of claim 11 wherein the at least one alkyl polyglycoside comprises a composition wherein R is an alkyl group having from 10 to about 18 carbon atoms, m is 0, G is a glucose residue and r is a number of from about 1.1 to about 2.

13. A method of claim 12 wherein a viscosity reducing effective amount of the alkali metal chloride and alkyl polyglycoside is from about 0.25% to about 5% by weight of the alkyl polyglucoside, and about 0.5 to 5% by weight of an alkali metal chloride.

14. A method of claim 13 wherein the alkyl polyglucoside has a DP in the range of about 1.1 to about 2 and the alkali metal chloride is selected from the group consisting of sodium chloride, potassium chloride and mixtures thereof.

* * * * *